United States Patent
Simpson

(10) Patent No.: US 6,803,495 B2
(45) Date of Patent: Oct. 12, 2004

(54) POLYURETHANE FOAM COMPOSITION AND METHOD OF MANUFACTURE THEREOF

(75) Inventor: Scott S. Simpson, Woodstock, CT (US)

(73) Assignee: World Properties, Inc., Lincolnwood, IL (US)

( * ) Notice: Subject to any disclaimer, the term of this patent is extended or adjusted under 35 U.S.C. 154(b) by 423 days.

(21) Appl. No.: 09/892,731

(22) Filed: Jun. 27, 2001

(65) Prior Publication Data

US 2002/0062097 A1 May 23, 2002

Related U.S. Application Data

(60) Provisional application No. 60/214,623, filed on Jun. 28, 2000.

(51) Int. Cl.[7] .............................. A61F 13/00; C08J 9/00; C08J 9/06
(52) U.S. Cl. ........................... 602/46; 602/602; 602/41; 521/50; 521/56
(58) Field of Search .............................. 602/41, 42, 46; 428/36.5, 311.11, 311.71, 314.8; 521/50, 51–60, 75, 134

(56) References Cited

U.S. PATENT DOCUMENTS

| | | | |
|---|---|---|---|
| 2,591,844 A | 4/1952 | Macripo | 40/86 |
| 2,602,783 A | 7/1952 | Simon et al. | 260/2.5 |
| 2,621,166 A | 12/1952 | Schmidt et al. | 260/75 |
| 2,698,838 A | 1/1955 | Simon et al. | 260/2.5 |
| 2,729,618 A | 1/1956 | Muller et al. | 260/75 |
| 2,779,689 A | 1/1957 | Reis, Jr. | 117/104 |
| 2,808,391 A | 10/1957 | Pattison | 260/77.5 |
| 2,811,493 A | 10/1957 | Simon et al. | 260/2.5 |
| 2,833,730 A | 5/1958 | Barthel, Jr. | 260/2.5 |
| 2,834,748 A | 5/1958 | Bailey et al. | 260/42 |
| 2,846,458 A | 8/1958 | Haluska | 260/448.2 |
| 2,850,476 A | 9/1958 | Seeger | 260/45.4 |
| 2,866,744 A | 12/1958 | Askey et al. | 208/65 |
| 2,866,762 A | 12/1958 | Brochhagen et al. | 260/2.5 |
| 2,868,824 A | 1/1959 | Haluska | 260/448.2 |
| 2,870,097 A | 3/1959 | Pattison | 260/2 |
| 2,878,601 A | 8/1959 | Burmeister et al. | 38/77 |
| 2,877,212 A | 10/1959 | Seligman | 260/77.5 |
| 2,901,473 A | 11/1959 | Steinemann | 260/146 |
| 2,911,390 A | 12/1959 | Smith | 260/77.5 |
| 2,917,480 A | 12/1959 | Bailey et al. | 260/42 |
| 2,921,915 A | 1/1960 | Brochhagen et al. | 260/2.5 |
| 2,962,524 A | 11/1960 | Hostettler et al. | 260/484 |

(List continued on next page.)

FOREIGN PATENT DOCUMENTS

| | | |
|---|---|---|
| BE | 905570 A | 4/1987 |
| BE | 905798 A | 5/1987 |
| GB | 733624 | 7/1955 |
| GB | 1037907 | 8/1966 |
| GB | 1585628 | 11/1981 |
| SU | 1822796 A1 | 6/1993 |

OTHER PUBLICATIONS

Boretos, J. W., "Cellular Polymers for Medical Use: The Vital Role of Porosity and Permeability", (1984) Cellular Polymers 3, pp. 345–358.

*Primary Examiner*—Kim M. Lewis
(74) *Attorney, Agent, or Firm*—Cantor Colburn LLP

(57) ABSTRACT

An open-celled polyurethane foam formed from a composition comprising an active hydrogen-containing component, an organic polyisocyanate component having an average isocyanate functionality of 2.00 to 2.25, a surfactant component, and a catalyst. The foam has a thickness of about 6 to about 20 mils; a density of about 10 to about 50 pcf; an average cell diameter of about 25 to about 80 microns; and cell openings having an average diameter of about 1 to about 25 microns, wherein the ratio of average cell diameter to average cell opening diameter is about 3 to about 10; a water vapor transmission rate of greater than about 1000 grams per square meter per day, and which do not leak water or similar fluids. Such foams find particular utility as backings for bandages.

30 Claims, 4 Drawing Sheets

U.S. PATENT DOCUMENTS

| | | | |
|---|---|---|---|
| 3,772,224 A | 11/1973 | Marlin et al. | 260/2.5 BD |
| 3,821,130 A | 6/1974 | Barron et al. | 260/2.5 BD |
| 3,947,386 A * | 3/1976 | Prokai et al. | 260/2.5 |
| 3,949,742 A | 4/1976 | Nowakowski | 128/155 |
| 3,975,567 A | 8/1976 | Lock | 428/315 |
| 3,978,266 A | 8/1976 | Lock | 428/315 |
| 3,978,855 A | 9/1976 | McRae et al. | 128/156 |
| 4,137,200 A | 1/1979 | Wood et al. | 521/159 |
| 4,233,969 A | 11/1980 | Lock et al. | 128/156 |
| 4,362,825 A | 12/1982 | Grabhoefer et al. | 521/172 |
| 4,550,126 A | 10/1985 | Lorenz | 521/159 |
| 4,603,076 A | 7/1986 | Bowditch et al. | 428/246 |
| 4,655,210 A | 4/1987 | Edenbaum et al. | 128/156 |
| 4,683,877 A | 8/1987 | Ersfeld et al. | 128/90 |
| 4,730,611 A | 3/1988 | Lamb | 128/156 |
| 4,733,659 A | 3/1988 | Edenbaum et al. | 128/156 |
| 4,738,257 A | 4/1988 | Meyer et al. | 128/156 |
| 4,906,240 A | 3/1990 | Reed et al. | 604/307 |
| 5,065,752 A | 11/1991 | Sessions et al. | 128/156 |
| 5,088,483 A | 2/1992 | Heinecke | 602/46 |
| 5,292,777 A | 3/1994 | DesMarais et al. | 521/64 |
| 5,409,472 A | 4/1995 | Rawlings et al. | 604/307 |
| 5,571,079 A | 11/1996 | Bello et al. | 602/46 |
| 5,571,529 A | 11/1996 | Cheong | 424/445 |
| 5,718,674 A | 2/1998 | Penrose | 602/46 |
| 5,733,945 A | 3/1998 | Simpson | 521/124 |
| 5,782,787 A | 7/1998 | Webster | 602/46 |
| 5,844,013 A | 12/1998 | Kenndoff et al. | 521/137 |
| 5,973,221 A | 10/1999 | Collyer et al. | 602/46 |

* cited by examiner

POLYURETHANE FOAM COMPOSITION AND METHOD OF MANUFACTURE THEREOF

CROSS REFERENCE TO RELATED APPLICATION

This application claims priority to and incorporates by reference U.S. Provisional Application Ser. No. 60/214,623 filed Jun. 28, 2000.

BACKGROUND OF THE INVENTION

1. Field of the Invention

This invention relates generally to flexible polyurethane foams. More particularly, this invention relates to thin, flexible polyurethane foams that are useful as backing materials in bandages.

2. Brief Description of the Related Art

Polyurethane foams are useful materials for a wide variety of applications, including as backing materials in bandages for wound care. Such foams may have densities in the range from about 10 to about 50 pounds per cubic foot (pcf) (about 160 to about 801 kilograms per cubic meter (kcm)). In order to act as an effective backing material, thin films of the polyurethane foams should have a good surface feel and be easily stretchable, yet also have high tensile and tear strength to prevent tearing during use. It is also important that the foams have a high water vapor transmission rate while at the same time a low liquid permeability to prevent leakage into or from the wound.

The preparation of flexible polyurethane compositions for use in wound care is generally known, as evidenced by the prior art. Hydrophilic, water-absorptive polyurethane materials specifically for the treatment of burns are disclosed in U.S. Pat. Nos. 3,978,266 and 4,233,969 to Lock. Other hydrophilic, water-absorptive materials are disclosed in U.S. Pat. No. 3,648,692 to Wheeler, U.S. Pat. No. 3,927,669 to Glatt, U.S. Pat. No. 4,550,126 to Lorenz, U.S. Pat. Nos. 4,655,210 and 4,733,659 to Edenbaum, et al., U.S. Pat. No. 5,844,013 to Kenndoff et al., and U.S. Pat. No. 5,292,777 to DesMarais et al. The purpose of such materials is primarily as sponges, medicament carriers, and surgical dressings for the absorption of liquid wound exudate.

Use of flexible polyurethane foams as backing layers has also been described. For example, U.S. Pat. No. 5,844,013 teaches the preparation of hydrophilic polyurethane gel foams, but with a polyurethane sheet as a backing. U.S. Pat. No. 4,738,257 to Meyer et al. discloses a highly elastic, porous polyurethane foam used as a backing material, which stretches upon absorption of water by a skin-contacting layer. Flexible polyurethane backing layers or tapes are also generally disclosed in U.S. Pat. No. 4,362,825 to Grabhoefer et al. and U.S. Pat. No. 3,665,918 to Lindquist et al. Grabhoefer et al discloses blown polyurethane foams manufactured using polyester polyols having OH numbers from 40 to 80 and molecular weights in the range from 1500 to 5000. The compositions are fairly specific, requiring, e.g., 1,4-butanediol. The foams of Lindquist require an extra manufacturing step, i.e., permanent compression of the foam to less than about 50 percent of its original thickness. Each of the foregoing is incorporated herein by reference.

While a number of these prior art foams meet at least some of the requirements for bandages, it has heretofore been difficult to impart good or excellent water vapor transmission rates and low water permeability to such foams, while at the same time maintaining the desired characteristics of easy stretchability, tensile and tear strength, and surface feel. It is especially difficult to obtain the requisite combination of high tensile and tear strengths while retaining easy stretchability and conformability. Because of these or other deficiencies such as ease of manufacture, these prior art foams are not ideal for use as bandage backing materials. Consequently, there remains a need for polyurethane foam compositions which have low liquid permeable but which transmit water vapor, and which still retain the required degree of easy stretchability, tensile strength, tear strength, and surface feel.

SUMMARY OF THE INVENTION

The above-discussed and other drawbacks and deficiencies of the prior art are overcome or alleviated by a composition for the formation of a soft, flexible polyurethane foam, comprising an active hydrogen-containing component, an organic polyisocyanate component having an isocyanate functionality of 2.00 to 2.25, a surfactant, and a catalyst component, wherein the OH number of the composition is from about 100 to about 180, and wherein formed foam has a density in the range from about 20 to about 5025 pcf (about 16 to about 801 kcm); the average cell size of the foam is about 20 to about 60 micrometers (microns); the typical cell openings are about 5 to about 25 microns, wherein the ratio between cell average diameter and cell opening average diameter is from about 3 to about 10; and the molecular weight between crosslinks is in the range from about 3000 to about 10,000. The individual cells are furthermore preferably substantially spherical.

Such foams are easily stretchable and conformable and have high water vapor transmission and low liquid permeability, while at the same time excellent tensile and tear strength, as well as acceptable surface feel. Because of the foregoing numerous features and advantages, the materials described are especially suitable for use as backing materials for bandages. The above-discussed and other features and advantages will be appreciated and understood by those skilled in the art from the following FIGURES and detailed description.

BRIEF DESCRIPTION OF THE FIGURES

The invention is further illustrated by the following figures, which are not to be construed as limitations.

DESCRIPTION OF THE PREFERRED EMBODIMENTS

Figure 1:
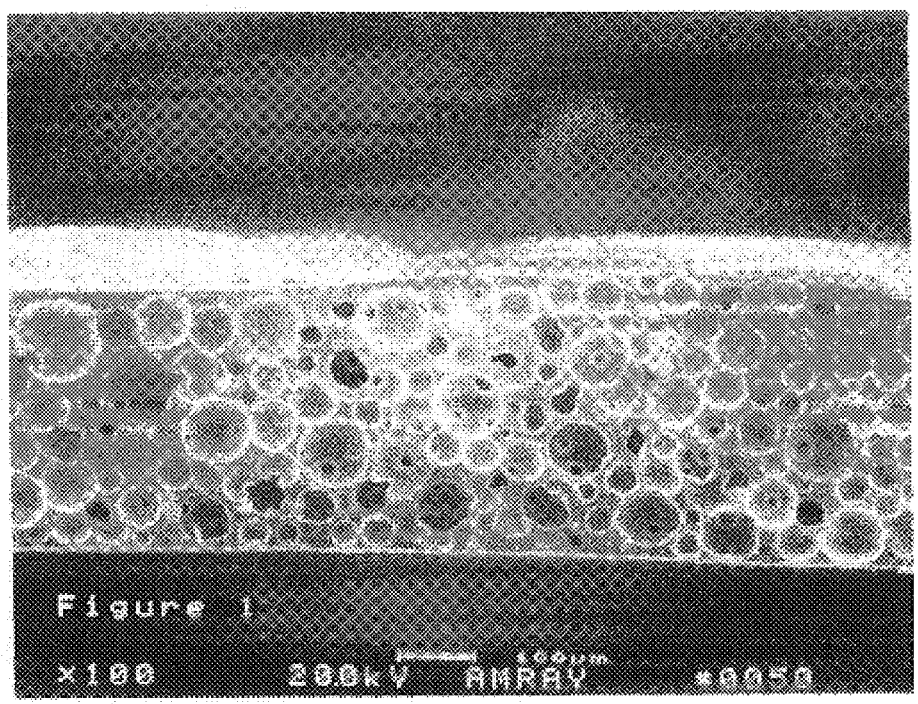
FIG. 1 is a cross-sectional SEM at 100× of the present foam.

A composition for the formation of a soft, flexible, yet strong polyurethane foam having high water vapor transmission and low liquid permeability has an OH number from about 100 to about 180, and comprises a mixture of:

an organic polyisocyanate component having an average isocyanate functionality of 2.00 to 2.25, an active hydrogen-containing component substantially reactive with said polyisocyanate;

an organosilicone surfactant for structurally stabilizing the froth produced according to step (2) below, during the period that the liquid phase of said froth is chemically stable and until said froth is cured to produce a cured foam, and a catalyst having substantial catalytic activity in the curing of said mixture.

The process of forming the foam comprises first forming the above-described mixture; secondly, substantially uniformly dispersing inert gas throughout the mixture by mechanical beating of said mixture to form a heat curable froth which is substantially structurally and chemically stable, but workable at ambient conditions, wherein said froth is free of auxiliary blowing agents; and thirdly heating said froth to form a cured polyurethane foam, any further expansion of said froth during heat curing being substantially only thermal expansion of said inert gas employed. Such compositions and methods of manufacture thereof are described generally in U.S. Pat. No. 3,772,224 to Marlin et al., which is incorporated by reference herein.

The organic polyisocyanate components preferably are those having the general formula:

$$Q(NCO)_i$$

wherein i is an integer of two or more and Q is an organic radical having the valence of i. In an important feature of the present composition, the average value of i is low, i.e., in the range from 2 to 2.25. Use of polyisocyanates having a low functionality (in conjunction with the polyol component described below) unexpectedly results in improved toughness for the cured polyurethane foams.

Q can be a substituted or unsubstituted hydrocarbon group (i.e., an alkylene or an arylene group). Q can be a group having the formula $Q^1$—Z—Q1 wherein $Q^1$ is an alkylene or arylene group and Z is —O—, —O—$Q^1$—, —CO—, —S—, —S—$Q^1$—S—, or —SO$_2$—. Examples of such compounds include hexamethylene diisocyanate, 1,8-diisocyanato-p-methane, xylyl diisocyanate, diisocyanatocyclohexane, phenylene diisocyanates, tolylene diisocyanates, including 2,4-tolylene diisocyanate, 2,6-tolylene diisocyanate, and crude tolylene diisocyanate, bis(4-isocyanatophenyl)methane, chlorophenylene diisocyanates, diphenylmethane-4,4'-diisocyanate (also known as 4,4'-diphenyl methane diisocyanate, or MDI) and adducts thereof, naphthalene-1,5-diisocyanate, triphenylmethane-4,4',4"-triisocyanate, and isopropylbenzene-alpha-4-diisocyanate and polymeric isocyanates such as polymethylene polyphenylisocyanate.

While the aforementioned isocyanates wherein i has a valence of two, for example 4,4'-diphenyl methane diisocyanate (MDI), may have been mentioned in the related art as being preferred for use in the formation of polyurethane foams, those of ordinary skill in the art are aware that commercial formulations of such isocyanates have an average value of i of 2.3 and above. Higher values of i have heretofore generally been used for ease of handling and/or cost. It has unexpectedly been discovered by the inventors hereof that restricting the value of i to 2.0 to 2.25 results in foams with a variety of desirable properties, including toughness. A preferred polyisocyanate is a polymeric diphenyl methane diisocyanate having an average value of i of 2.25 and a percent NCO of 27.6. This polyisocyanate is available from Bayer under the trade name Baytuft 757.

The amount of polyisocyanate employed will vary slightly depending upon the nature of the polyurethane being prepared. In general, the total —NCO equivalent to total active hydrogen equivalent should be such as to provide a ratio of 0.8 to 1.2 equivalents of —NCO per equivalent of active hydrogen, e.g., hydroxyl hydrogen, of the active hydrogen reactant, and preferably a ratio of about 1.0 to 1.05 equivalents of —NCO per active hydrogen.

The active hydrogen-containing component includes polyhydroxyl-containing compounds, such as hydroxyl-terminated polyhydrocarbons (U.S. Pat. No. 2,877,212); hydroxyl-terminated polyformals (U.S. Pat. No. 2,870,097); fatty acid triglycerides (U.S. Pat. Nos. 2,833,730 and 2,878,601); hydroxyl-terminated polyesters (U.S. Pat. Nos. 2,698,838, 2,921,915, 2,591,884, 2,866,762, 2,850,476, 2,602,783, 2,729,618, 2,779,689, 2,811,493, and 2,621,166); hydroxymethyl-terminated perfluoromethylenes (U.S. Pat. Nos. 2,911,390 and 2,902,473); polyalkylene ether glycols (U.S. Pat. No. 2,808,391; British Pat. No. 733,624); polyalkylene ether glycols (U.S. Pat. No. 2,808,391; British Pat. No. 733,624); polyalkylenearylene ether glycols (U.S. Pat. No. 2,808,391); and polyalkylene ether triols (U.S. Pat. No. 2,866,774).

Especially preferred polyhydroxyl-containing compounds are the polyether polyols obtained by the chemical addition of alkylene oxides, such as ethylene oxide, propylene oxide and mixtures thereof, to water or polyhydric organic compounds, such as ethylene glycol, propylene glycol, trimethylene glycol, 1,2-butylene glycol, 1,3-butanediol, 1,4-butanediol, 1,5-pentanediol, 1,2-hexylene glycol, 1,10-decanediol, 1,2-cyclohexanediol, 2-butene-1,4-diol, 3-cyclohexene-1,1-dimethanol, 4-methyl-3-cyclohexene-1,1-dimethanol, 3-methylene-1,5-pentanediol, diethylene glycol, (2-hydroxyethoxy)-1-propanol, 4-(2-hydroxyethoxy)-1-butanol, 5-(2-hydroxypropoxy)-1-pentanol, 1-(2-hydroxymethoxy)-2-hexanol, 1-(2-hydroxypropoxy)-2-octanol, 3-allyloxy-1,5-pentanediol, 2-allyloxymethyl-2-methyl-1,3-propanediol, [4,4-pentyloxy)-methyl]-1,3-propanediol, 3-(o-propenylphenoxy)-1,2-propanediol, 2,2'-diisopropylidenebis(p-phenyleneoxy)diethanol, glycerol, 1,2,6-hexanetriol, 1,1,1-trimethylolethane, 1,1,1-trimethylolpropane, 3-(2-hydroxyethoxy)-1,2-propanediol, 3-(2-hydroxypropoxy)-1,2-propanediol, 2,4-dimethyl-2-(2-hydroxyethoxy)-methylpentanediol-1,5; 1,1,1-tris[2-hydroxyethoxy) methyl]-ethane, 1,1,1-tris[2-hydroxypropoxy)-methyl]propane, diethylene glycol, dipropylene glycol, pentaerythritol, sorbitol, sucrose, lactose, alpha-methylglucoside, alpha-hydroxyalkylglucoside, novolac resins, and the like. The alkylene oxides employed in producing polyoxyalkylene polyols normally have from 2 to 4 carbon atoms. Propylene oxide and mixtures or propylene oxide with ethylene oxide are preferred. The polyols listed above can be used per se as the active hydrogen compound.

A preferred class of polyether polyols is represented generally by the following formula $$R[(OCH_nH_{2n})_zOH]_a$$

wherein R is hydrogen or a polyvalent hydrocarbon radical; a is an integer (i.e., 1 or 2 to 6 to 8) equal to the valence of R, n in each occurrence is an integer from 2 to 4 inclusive (preferably 3) and z in each occurrence is an integer having a value of from 2 to about 200, preferably from 15 to about 100.

Additional active hydrogen-containing compounds are the polymers of cyclic esters. The preparation of the cyclic ester polymers from at least one cyclic ester monomer is well documented in the patent literature as exemplified by U.S. Pat. Nos. 3,021,309 through 3,021,317; 3,169,945; and 2,962,524. Suitable cyclic ester monomers include but are not limited to delta-valerolactone; epsilon-caprolactone; zeta-enantholactone; the monoalkyl-valerolactones, e.g., the monomethyl-, monoethyl-, and monohexyl-valerolactones.

Cyclic ester/alkylene oxide copolymers can also be prepared by reacting a mixture comprising cyclic ester and alkylene oxide monomers, an interfacial agent such as a solid, relatively high molecular weight poly(vinylstearate) or lauryl methacrylate/vinyl chloride copolymer (reduced viscosity in cyclohexanone at 30° C. of from about 0.3 to about 1.0), in the presence of an inert normally-liquid saturated aliphatic hydrocarbon vehicle such as heptane and phosphorus pentafluoride as the catalyst therefor, at an elevated temperature, e.g., about 80° C.

Another useful type of active hydrogen-containing materials include the polymer/polyol compositions obtained by polymerizing ethylenically unsaturated monomers in a polyol as described in U.S. Pat. No. 3,383,351, the disclosures of which is incorporated herein by reference. Suitable monomers for producing such compositions include acrylonitrile, vinyl chloride, styrene, butadiene, vinylidene chloride and other ethylenically unsaturated monomers as identified and described in the above-mentioned U.S. patent. Suitable polyols include those listed and described hereinabove and in the U.S. patent. The polymer/polyol compositions can contain from 1 to about 70 weight percent, preferably about 5 to about 50 weight percent, and most preferably about 10 to about 40 weight percent monomer polymerized in the polyol. Such compositions are conveniently prepared by polymerizing the monomers in the selected polyol at a temperature of 40 C. to 150 C. in the presence of a free radical polymerization catalyst such as peroxides, persulfates, percarbonate, perborates, and azo compounds.

Preferred active hydrogen-containing components are polyol mixtures comprising very low molecular weight polyols as chain extenders or crosslinking agents. Exemplary chain extenders and cross-linking agents are low molecular weight diols, such as alkane diols and dialkylene glycols, and/or polyhydric alcohols, preferably triols and tetrols, having a molecular weight from about 200 to 400. The chain extenders and cross-linking agents are used in amounts from about 0.5 to about 20 percent by weight, preferably from about 10 to 15 percent by weight, based on the total weight of the polyol component.

Preferred active hydrogen-containing components further comprise higher molecular weight polyether polyols and polyester polyols. Preferred polyether polyols include polyoxyalkylene diols and triols, and polyoxyalkylene diols and triols with polystyrene and/or polyacrylonitrile grafted onto the polymer chain, and mixtures thereof. Preferred polyester polyols are based on caprolactone.

In one preferred embodiment, the polyol component comprises one or a mixture of a low molecular weight diol; one or a mixture of a polyether oxide diol having a molecular weight in the range from about 250 to about 750, one or a mixture of a polyester diol having a molecular weight in the range from about 400 to about 600, and one or a mixture of a polyether diol having a molecular weight in the range from about 1000 to about 3000.

In another preferred embodiment, the polyol component comprises one or a mixture of a very low molecular weight (below about 200) diol, including but not being limited to, dipropylene glycol, 1,4-butanediol, 2-methyl-1,3-propanediol, and 3-methyl-1,5-pentane diol; one or a mixture of a polypropylene oxide diol having a molecular weight in the range from about 400 to about 500; one or a mixture of a polycaprolactone-based diol having a molecular weight in the range from about 400 to about 600; and one or a mixture of a polypropylene oxide triol having polystyrene and polyacrylonitrile grafts having a molecular weight in the range from about 2500 to about 3500.

There are a number of preferred embodiments of this invention that can be tailored to the specific bandage application depending on the thickness, softness, stretchability, and water vapor transmission levels desired. In all cases the toughness of these backing materials needs to be maximized making the foams of this invention desireable for bandage applications.

In general, the hydroxyl numbers of the polyols or mixtures thereof, including other cross-linking additives, fillers, surfactants, catalysts and pigments, if employed, can range from about 90 to about 170, preferably from about 100 to about 160, and most preferably from about 120 to about 140. The hydroxyl number is defined as the number of milligrams of potassium hydroxide required for the complete neutralization of the hydrolysis product of the fully acetylated derivative prepared from 1 gram of polyol or mixtures of polyols with or without other cross-linking additives used in the invention. The hydroxyl number can also be defined by the equation:

$$OH = \frac{56.1 \times 1000 \times f}{M.W.}$$

wherein OH is the hydroxyl number of the polyol, f is the average functionality, that is average number of hydroxyl groups per molecule of polyol, and M. W. is the average molecular weight of the polyol.

The particular polyol components, i.e., the molecular weights and the hydroxyl number are further selected so as to provide a molecular weight between crosslinks of about 3,000 to about 10,000, preferably about 4,000 to about 7,000. The molecular weight between crosslinks (Mc) is calculated by dividing the total weight of material by the sum of the moles of each reactive component each multiplied by its functionality minus 2.

A wide variety of organosilicone surfactants can be employed for purposes of stabilizing the froth. A preferred stabilizer is an organosilicone copolymer consisting essentially of $SiO_2$ (silicate) units and $(CH_3)_3SiO_{0.5}$ (trimethylsiloxy) units in a molar ratio of silicate to trimethylsiloxy units of about 0.8:1 to about 2.2:1, preferably about 1:1 to about 2.0:1. Another preferred organosilicone surfactant stabilizer is a partially cross-linked siloxane-polyoxyalkylene block copolymer and mixtures thereof wherein the siloxane blocks and polyoxyalkylene blocks are linked by silicon to carbon, or by silicon to oxygen to carbon, linkages. The siloxane blocks are comprised of hydrocarbon-siloxane groups and have an average of at least two valences of silicon per block combined in said linkages. At least a portion of the polyoxyalkylene blocks are comprised of oxyalkylene groups and are polyvalent, i.e., have at least two valences of carbon and/or carbon-bonded oxygen per block combined in said linkages. Any remaining polyoxyalkylene blocks are comprised of oxyalkylene groups and are monovalent, i.e., have only one valence of carbon or carbon-bonded oxygen per block combined in said linkages. Additionally, conventional organo polysiloxanepolyoxyalkylene block copolymers such as those described in U.S. Pat. Nos. 2,834,748, 2,846,458, 2,868,824, 2,917,480 and 3,057,901 can be employed. Partially crosslinked copolymers and the trimethyisiloxysilicate copolymers are more useful with the non-prepolymer polyisocyanates; such as the monomeric polyisocyanates, for example, toluene diisocyanate. The amount of the organosilicone polymer employed as a foam stabilizer can vary over wide limits, e.g., from about 0.5 weight parts to 10 weight parts or greater, per hundred weight parts of the active hydrogen component. Preferably, the amount of organosilicone copolymer present in the foam formulations varies from about 1.0 weight parts to about 6.0 parts on the same basis.

Catalysts include various inorganic metal compounds and metal compounds that include certain organic groups. Metal acetyl acetonates are preferred, including metals such as aluminum, barium, cadmium, calcium, cerium (III), chromium (III), cobalt (II), cobalt (III), copper (II), indium, iron (II), lanthanum, lead (II), manganese (II), manganese (III), neodymium, nickel (II), palladium (II), potassium, samarium, sodium, terbium, titanium, vanadium, yttrium, zinc and zirconium. One commonly used catalyst is bis(2,4-pentanedionate) nickel (II) (also known as nickel acetylacetonate or diacetylacetonate nickel) and derivatives thereof such as diacetonitrilediacetylacetonato nickel, diphenylnitrilediacetylacetonato nickel, bis(triphenylphosphine)-diacetyl acetylacetonato nickel, and the like. In addition, tin catalysts such as stannous acylates (i.e., dialkyl tin salts of carboxylic acids, e.g., dibutyl tin dilaurate) can be used in the presence of the trimethylsiloxysilicate copolymer surfactants described above.

Iron acetyl acetonate is particularly preferred, due to its relative stability, good catalytic activity and lack of toxicity. The metal acetyl acetonate is most conveniently added by predissolution in a suitable solvent such as dipropylene glycol or other hydroxyl containing compound which will then participate in the reaction and become part of the final product. Added to the metal acetyl acetonate is acetyl acetone (2,4-pentanedione), as disclosed in U.S. Pat. No. 5,733,945, which is incorporated herein be reference. It has been discovered that the acetyl acetone can be used to delay or inhibit the normally reactive metal acetyl acetonate at the lower temperatures needed to achieve proper mixing and casting. In other words, the acetyl acetone provides heat latency, which allows time for the required mixing, casting and other procedures, and avoids deleterious premature curing during low temperature processing. However, as the material is cured in the several heating zones and the temperature of the urethane mixture rises, the acetyl acetone is driven off. With the acetyl acetone removed together with its associated delaying function, the metal acetyl acetonate is allowed to resume its normally high reactivity and provide a very high level of catalysis at the end of the polyurethane reaction. This high reactivity late in the processing cycle is advantageous and provides improved physical properties such as compression set. In general, the ratio of metal acetyl acetonate to acetyl acetone is about 2:1 on a weight basis. The amount of catalyst present in the liquid phase is preferably in the range of 0.03 to 3.0 weight parts per hundred weight parts of the active hydrogen compound.

The liquid phase can contain other ingredients such as dyes, fillers, pigments, and other materials for providing desired effects. Small amounts of an auxiliary blowing agent can be employed. For example, high boiling fluorocarbons, e.g., boiling above about 40° C. can be used. Very small amounts of water can be employed. Specific fluorocarbons include the Ucon fluorocarbons and Freons boiling above about 40° C., for example 1,1,2-trichloro-1,2,2-trifluoroethane and isomers of tetrachlorodifluoroethane, tetrachloromonofluoroethane, and the like. The auxiliary agent, although it is not necessary, can be employed for purposes of providing an added expansion during heat curing in those cases where such added expansion is desired.

An inert gas is incorporated into the liquid phase by mechanical beating of the liquid phase in high shear equipment such as a Hobart mixer or an Oakes mixer. Mechanical blowing is preferred, as it is more likely to lead to spherical cells than chemically blown foams. The gas phase of the novel froths is most preferably air because of its cheapness and ready availability. However, if desired, other gases can be used which are gaseous at ambient conditions and which are substantially inert or non-reactive with any component of the liquid phase. Such other gases include, for example, nitrogen, carbon dioxide and fluorocarbons that are normally gaseous at ambient temperatures. The gas can be introduced under pressure as in the usual operation of an Oakes mixer or it can be drawn in from the overlying atmosphere by the beating or whipping action as in a Hobart mixer. The mechanical beating operation preferably is conducted at pressures not greater than 100 to 200 p.s.i.g. It is significant, however, to note that conventional, readily available, mixing equipment is used and no special equipment is necessary. The amount of inert gas beaten into the liquid phase should be adequate to provide a froth having a density at ambient atmospheric pressure of less than about 30% to about 60% of the density of the liquid phase prior to frothing. The mechanical beating is conducted over a period of a few seconds in an Oakes mixer, or of 3 to 30 minutes in a Hobart mixer, or however long it takes to obtain the desired froth density in the mixing equipment employed.

The froth as it emerges from the mechanical beating operation is substantially chemically stable and is structurally stable but easily workable at ambient temperatures, e.g., about 15° C. to about 30° C. The consistency of the froth closely resembles the consistency of aerosol-dispensed shaving cream. The foams after cure are substantially or entirely open-celled.

The formed, cured foams have a density of about 20 to about 40 pcf, preferably about 25 to about 35 pcf, more preferably about 28 to about 32 pcf, and most preferably about 30 pcf. In a preferred feature, the foams formed from the above-described compositions are used in the form of films having a thickness from about 6 to about 20 mils. The water vapor transmission rate of such films in the up direction is greater than about 1000 grams per square meter per day ($g/m^2$/day), and preferably greater than about 1500 $g/m^2$/day. The foams do not leak liquid, however, and will maintain their shape when in contact with liquid.

In one embodiment having "normal" softness, the films have a thickness of about 8 to about 12 mils, more preferably about 10 to about 12 mils, and most preferably about 12 mils. In another embodiment having "normal" softness, the films have a thickness of about 14 to about 18 mils, more preferably about 15 to 17 mils, and most preferably about 16 mil. Although thin, each of these foams is also tough, as reflected by the preferred properties shown in Table 1 below. Further as shown in Table 1 below, the characteristics of a "softer" version of the foam is provided, preferably having a thickness of about 16 mils. This softer version provides even greater comfort, the tensile load at 20% elongation being less than about 40 psi.

TABLE 1

|  | 6–20 mils | Normal | | | | | | Softer |
|---|---|---|---|---|---|---|---|---|
|  |  | 8–12 mils | | | 14–18 mils | | | 16 mils |
| Property |  | Preferred | More preferred | Most preferred | Preferred | More preferred | Most preferred | Most preferred |
| Density, pcf | 20–40 | 20–40 | 25–35 | 28–32 | 20–40 | 25–35 | 28–32 | 28–32 |
| Tensile strength, psi | >200 | >350 | >375 | >400 | >300 | >325 | >350 | >150 |
| Elongation, % | >120 | >120 | >160 | >200 | >120 | >160 | >200 | >160 |
| Tear strength, pli | >10 | >15 | >20 | >20 | >15 | >20 | >20 | >20 |
| Tensile load at 20% elongation, psi | <100 | <70 | <60 | <50 | <70 | <60 | <50 | <35 |
| Up WVTR | >1000 | >1000 | >1500 | >2000 | >1000 | >1500 | >2000 | >2000 |
| Water Leakage | no | no | No | No | no | no | no | no |
| Down WVTR, | >1000 | >2000 | >4000 | >4000 | >2000 | >4000 | >4000 | >4000 |

Figure 2:
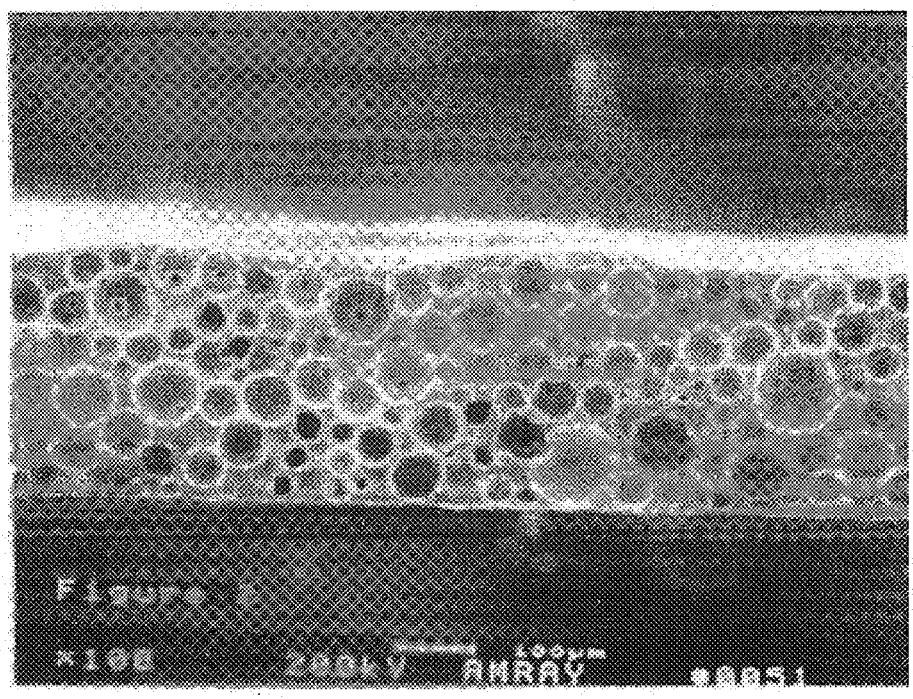
FIG. 2 is a cross-sectional SEM at 100× of another embodiment of the present foam.
Figure 3:
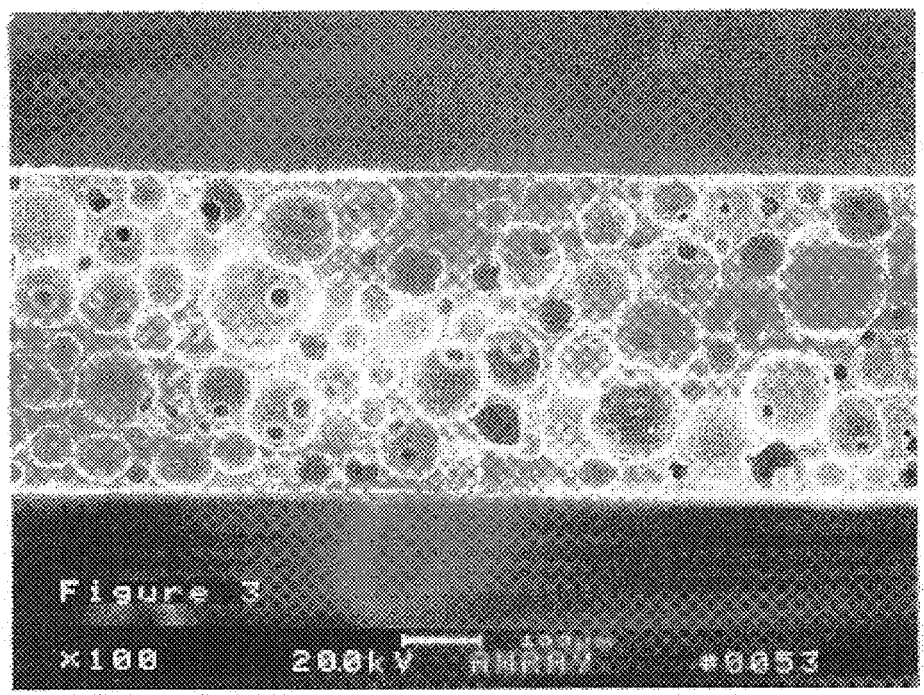
FIG. 3 is a cross-sectional SEM at 100× of another embodiment of the present foam.
Figure 4:
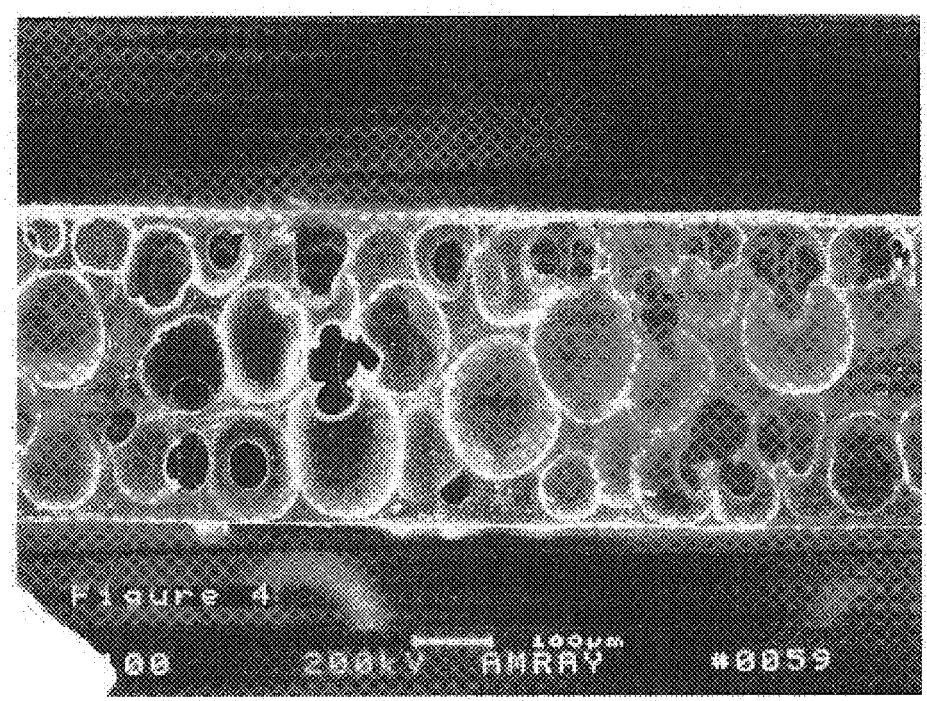
FIG. 4 is a cross-sectional SEM at 100× view of a prior art foam.
Figure 7:
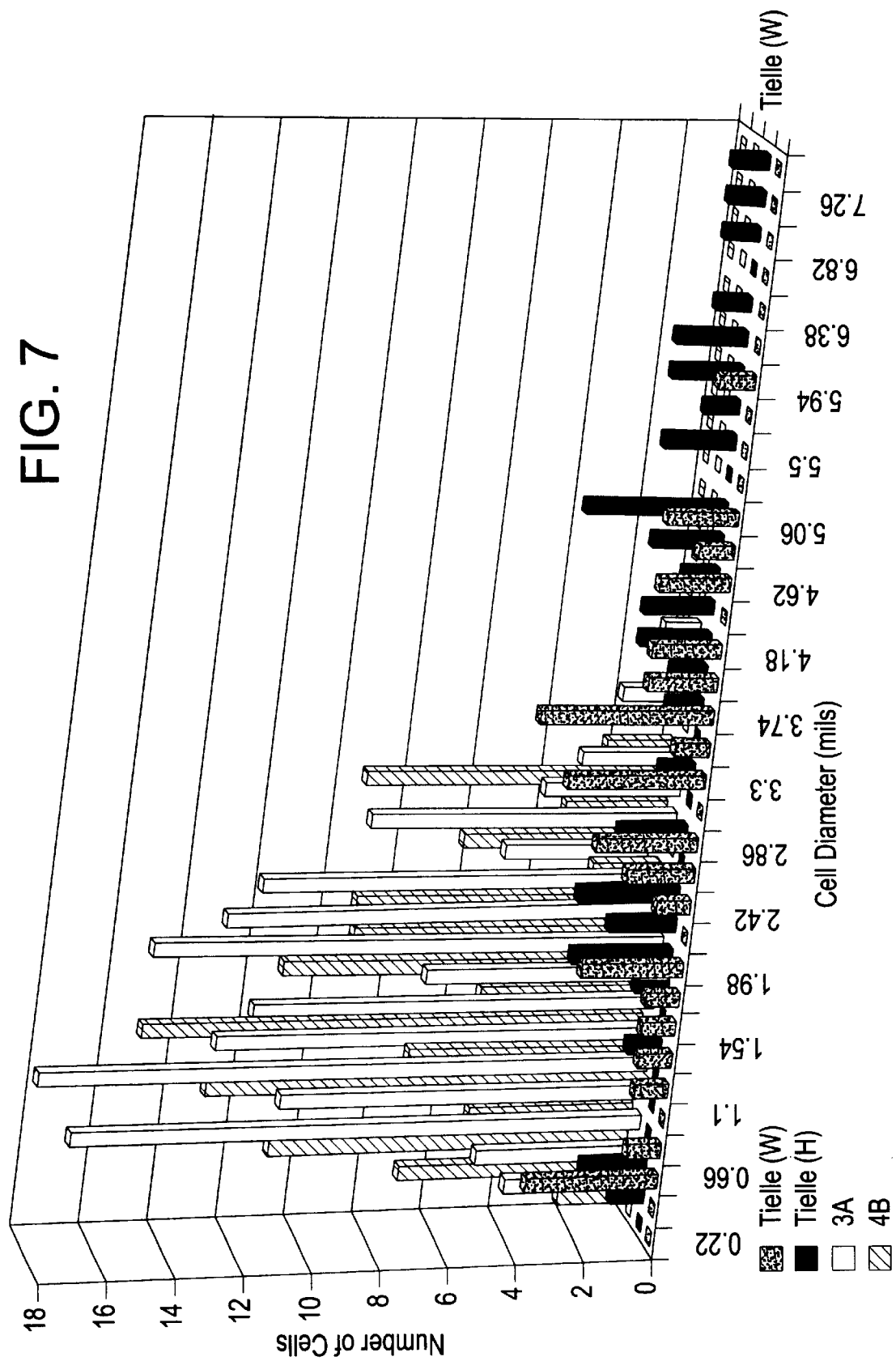
FIG. 7 is a three-dimensional bar chart showing the relative distribution of cell sizes (mils) of the present foam compared to the prior art.

Without being bound by theory, the advantageous physical properties of the foams is due at least in part to open cells with an appropriate range of cell opening sizes and with a slightly hydrophobic surface, which results in high water vapor transmission without allowing significant passage of liquids through the foam in either direction. Hydrophobicity is imparted in part by appropriate selection of the polyol components and surfactant. In addition, the cells are substantially uniform in size and substantially spherical in cross-section, as shown from cross-sectional scanning electron microscope (SEM) images of the inventive foams as shown in FIGS. 1–3. These properties likely arise from the fact that the foams are mechanically frothed. The uniform cell sizes and spherical cross-sections shown in FIGS. 1–3 are in distinct contrast to the cross-sectional SEM images of prior art foams used as backing materials for bandages as shown in FIG. 4. The larger, elongated cells of the prior art are likely created by chemical blowing, and create more direct paths for water, thereby allowing leakage through the foams. It can futher be seen from FIG. 7 that the present foams have a much narrower size distribution than the foams of the prior art.

The inventive foams accordingly comprise cells having an average diameter of less than about 70 microns, preferably about 1 to about 60 microns, and most preferably about 40 to about 60 micron. The cells furthermore have openings between the cells (pores) with an average diameter of less than about 40 microns, preferably about 1 to about 25 microns, more preferably about 5 to about 15 microns, and most preferably about 8 to about 15 microns. The ratio of average cell diameter to average cell pore diameter is in the range of about 3 to about 10, preferably about 3 to about 5, and most preferably about 4.

It may also be seen that the top surface of the foams shown in FIGS. 1 and 2 respectively (Examples 3A and 4B) are slightly irregular. This irregularity arises from casting the composition onto an embossed surface, thereby providing a more aesthetically pleasing appearance and feel to the backing. FIG. 3 (Example 5A) shows that a smooth surface may be obtained by casting onto a smooth surface.

Figure 6:
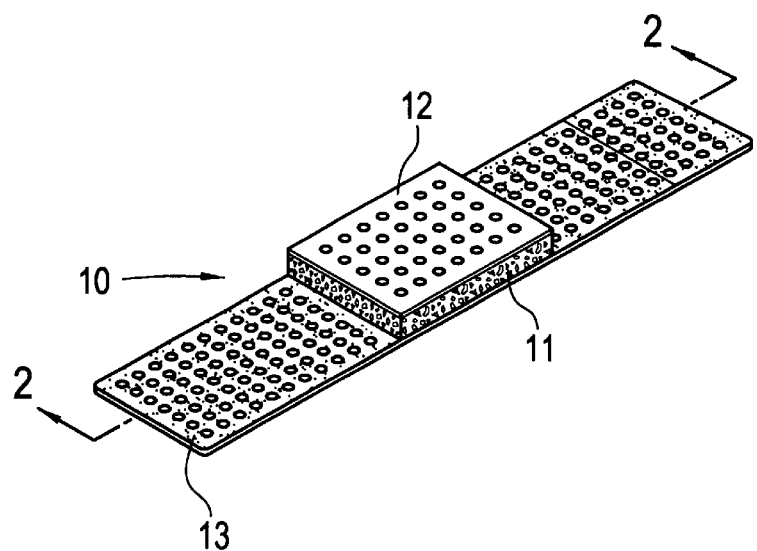
FIG. 6 is a plan view of a bandage using the present polyurethane foam.
Figure 5:
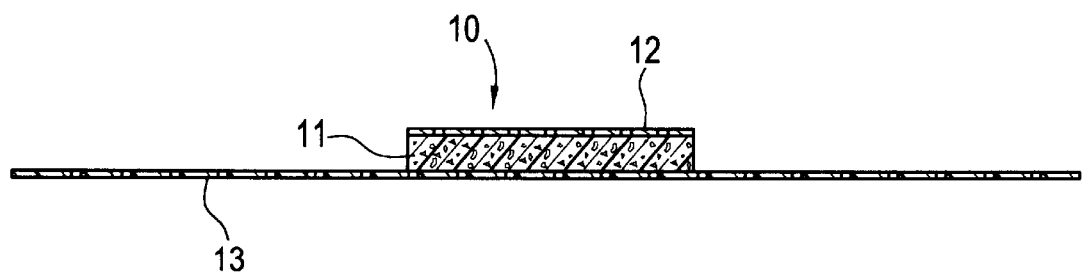
FIG. 5 is a schematic cross-sectional view of a bandage using the present polyurethane foam.

With reference now to FIGS. 5 and 6 simultaneously, the bandage construction, identified generally at 10 is seen to include a pad 11 and pad backing 12, arranged on and affixed to the intermediate regions of an elongated strip or strip-like element 13. More particularly, the pad 11 is constructed of a material having a plurality of interconnected pores to hollow cells, which enables ready permeation, in the gas phase. The pad has a generally rectangular shape with a width dimension substantially identical to that of the strip-like element 13. A major surface of the pad is affixed to the flat surface of the strip in its central regions with the pad peripheral edges coextensive with the edges of the strip. Any suitable adhesive may be used for affixing the pad to the strip. Preferably, the adhesive is applied so as to not interfere with water vapor transmission. The pad backing 12 is preferably constructed of a thin sheet of the polyurethane of the present invention.

The polyurethane foams are further described by the following non-limiting examples:

EXAMPLES

Chemicals, sources, and descriptions are listed in Table 2 below.

TABLE 2

| Trade Name | Source | Description |
|---|---|---|
| E351 | BAYER | Polyethylene oxide capped polypropylene oxide diol, MW = 2800 |
| 1652 | BAYER | Polypropylene oxide triol, MW = 3000 |
| PPG 425 | BAYER | Polypropylene oxide diol, MW = 450 |
| PPG 1025 | Bayer | Polypropylene oxide diol, MW = 1000 |
| PPG 2000 | Bayer | Polypropylene oxide diol, MW = 2000 |
| MPDiol | Bayer | 2-methyl-1,3-propane diol (chain extender) |
| MPTD | Kuraray | 3-methyl-1,5-pentane diol (chain extender) |
| Niax 24-32 | Bayer | Polypropylene oxide diol with polystyrene and polyacrylonitrile grafts, MW = 2800 |
| TONE 0201 | Union Carbide | Polycaprolactone-based polyester diol, MW = 500 |
| DPG | — | Dipropylene glycol (diol chain extender) |
| NIAX 34-35 | Bayer | Polypropylene oxide triol with polystyrene and polyacrylonitrile grafts, MW = 3000 (polymer polyol) |
| L-5617 | Crompton/Osi | Silicone-based surfactant |
| 3A Sieves | UOP | Alkali metal alumino silicate, $K_{12}[(AlO_2)_{12}(SiO_2)_{12}] \cdot XH_2O$ (water absorption) |
| IRGANOX 1135 | Ciba | Hindered phenol (Antioxidant) |
| IRGANOX 5057 | Ciba | Aromatic amine (Antioxidant) |
| BHT | — | Butylated hydroxytoluene |

TABLE 2-continued

| Trade Name | Source | Description |
|---|---|---|
| | | (antioxidant) |
| Pigment | PAN Chemical | Colorant, in 34-45 polyol |
| Catalyst | — | Ferric acetyl acetonate and acetyl acetone in polyol |
| Papi 901 | DOW Chemical | Polymeric diphenyl methane diisocyanate, % NCO = 31.6, Average Functionality = 2.3 |
| 757 | Bayer | Polymeric diphenyl methane diisocyanate, % NCO = 27.6, Average Functionality = 2.2 |

Polyurethane foams having the five compositions (1–5) set forth in Table 3 below were produced as follows. All of the polyol components (active hydrogen component, catalyst and additives, Part A) were mixed and placed in a holding tank with agitation and under dry nitrogen. This mixture was than pumped at a controlled flow rate to a high shear Oakes-type mixing head. The isocyanate (Part B) was separately pumped into the mixing head. Dry air was introduced into the mixing head using a gas flow rate controller to adjust the flow so that the cured material had the desired density, generally about 30 pcf. After mixing and foaming, the composition was cast onto coated release paper that had been dried by passing it through a high air flow or infrared drying oven at 275–300° F. just prior to the point where the foam was introduced. The cast foam was then passed under a knife over roll (KOR) coater to spread the foam to the desired thickness. The cast foam was then passed through heated platens (400° F. upper, 250–375° F. lower) to cure, and cooled.

TABLE 3

| | Composition No. | | | | |
|---|---|---|---|---|---|
| Component | 1* | 2 | 3 | 4 | 5 |
| LHT-240 | | 0 | 2.4 | 2.4 | 0 |
| PPG425 | | 0 | 6.8 | 0 | 6.8 |
| PPG2025/PPG2000 | | 27.4 | 38.03 | 24.7 | 41.43 |
| DPG | | 10.8 | 9.1 | 11.1 | 8.1 |
| L-5617 | | 2.7 | 2.7 | 2.7 | 2.7 |
| Tone 0201 | | 10.8 | 10.8 | 10.8 | 10.8 |
| Catalyst | | 3.33 | 6 | 3.4 | 6 |
| Niax 34-45 | | 28.14 | 5.33 | 26.12 | 5.33 |
| Alumina | | 20.1 | 20.1 | 18.1 | 20.1 |
| 3A Sieves | | 2 | 4 | 4 | 4 |
| IRGANOX 1135 | | 0.12 | 0 | 0 | 0 |
| IRGANOX 5057 | | 0.03 | 0 | 0 | 0 |
| BHT | | 0 | 0.07 | 0 | 0.07 |
| Pigment | | 4.42 | 4.42 | 4.42 | 4.42 |

TABLE 3-continued

| | Composition No. | | | | |
|---|---|---|---|---|---|
| Component | 1* | 2 | 3 | 4 | 5 |
| Total Parts Isocyanate | 109.8 | 109.8 | 109.8 | 109.8 | 109.8 |
| PAPI 901 | 34.33 | | | | |
| 751A | | 41.2 | 42.8 | 43.1 | 39.36 |
| OH# | 126.7 | 132.7 | 138.1 | 138.9 | 126.9 |
| Mc | 4525 | 5262 | 5436 | 4646 | 6359 |

*Prior art foam from Rogers Corp.

Each of formulations 1–5 was cast to a thickness of 16 mils (Samples 1A, 2A, 3A, 4A, and 5A). Formulations 1–4 were also cast to a thickness of 10.5 to 13 mils (Samples 1B, 2B, 3B, and 4B). Each of these foams were tested as follows. Results are shown in Table 4.

Modulus as reflected by compression force deflection (CFD) was determined on an Instron using 2-inch by 2-inch die-cut samples stacked to a minimum of 0.250 inches, usually about 0.375 inches, and a 20,000 pound cell mounted in the bottom of the Instron. CFD was measured by calculating the force in pounds per square inch (psi) required to compress the sample to 25% of the original thickness.

Tensile strength and elongation were measured using an Instron fitted with a 50-pound load cell and using 10–20 pound range depending on thickness and density. Tensile strength (psi) is calculated as the amount of force per inch of width at the break divided by the sample thickness. Elongation is reported as percent extension.

Tear strength was measured using an Instron fitted with a 50-pound load cell and using a 2, 5, or 10-pound load range depending on sample thickness and density. Tear strength is calculated by dividing the force applied at tear by the thickness of the sample.

Tensile load to achieve 20% elongation (a measure of stretchability) was measured in the same way as tensile strength in which the tensile load at the point of 20% elongation is calculated from the load cell data.

Up water vapor transmission (Up WVTR) was obtained by measuring the amount of water that evaporates through a sample of the foam covering a reservoir at 37° C. Permeability to water (Down WVTR) was measured by turning the sample and water reservoir upside down such that the water is in direct contact with the surface of the foam. The sample is also checked for evidence of water leakage using the Down WVTR method at room temperature. If a sample shows water leakage the Down WVTR value is not reported.

TABLE 4

| Properties | 1A* | 2A | 3A | 4A | 5A | 6** | 1B* | 2B | 3B | 4B |
|---|---|---|---|---|---|---|---|---|---|---|
| Thickness, mils | 16 | 16 | 16 | 16 | 16 | 15 | 13 | 10 | 11 | 10.5 |
| Density, pcf | 30.1 | 30.3 | 30.3 | 29.2 | 30.0 | 23.8 | 29.4 | 29.0 | 29.5 | 30.3 |
| CFD, psi | 44.7 | 50.0 | 27.9 | 53.1 | 20.0 | 47.6 | 41.7 | 40.2 | 26.7 | 54.1 |
| Tensile strength, psi | 327 | 416 | 352.8 | 433 | 199 | 229 | 335 | 379 | 303.8 | 417 |
| Elongation (%) | 115 | 167 | 229 | 145 | 205 | 280 | 115 | 161 | 211 | 134 |
| Tear strength, pli | 17.8 | 24.8 | 27.0 | 25.0 | 22.2 | 49 | 14.1 | 21.1 | 31.5 | 24.2 |
| Tensile load at 20% Elongation, psi | 61.9 | 51.4 | 45.5 | 64.2 | 26.1 | 42.0 | 58.1 | 52.2 | 43.1 | 67 |

TABLE 4-continued

| Properties | 1A* | 2A | 3A | 4A | 5A | 6** | 1B* | 2B | 3B | 4B |
|---|---|---|---|---|---|---|---|---|---|---|
| Up WVTR, g/m²/day | — | — | 2500 | — | 3814 | 2600 | — | — | — | 2100 |
| Down WVTR, g/m²/day | — | — | 6,000 | — | 15,910 | — | — | — | — | 4,200 |
| Water Leakage | — | — | No | — | No | Yes | — | — | — | No |

*Prior art polyurethane foam
**Prior art polyurethane foam

Foams 2A, 3A, and 4A in accordance with the present invention are 16 mils thick and have "normal" softness as reflected by tensile load at 20% elongation. Foam 5A in accordance with the present invention is also 16 mil thick, and is even softer. Foams 2B, 3B, and 4B in accordance with the present invention are 10 to 11 mils thick, and are also of "normal" softness. However, as may be seen by reference to the above table, the prior art foam in samples 1A (16 mil) and 1B (13 mil) has lower toughness compared to the foams of this invention, as shown by lower values in the tensile strength, elongation and tear strength compared to samples of this invention of equivalent softness. The prior art foam of sample 6 shows good physical properties but leaks water and also warped and stretched during the water leakage test.

While preferred embodiments have been shown and described, various modifications and substitutions may be made thereto without departing from the spirit and scope of the invention. Accordingly, it is to be understood that the present invention has been described by way of illustrations and not limitation.

What is claimed is:

1. A bandage, comprising
   an open-celled polyurethane foam, wherein the polyurethane foam has a density of about 20 to about 40 pounds per cubic foot, cells with an average diameter of about 20 to about 60 microns, and cell openings with an average diameter of about 1 to about 25 microns, wherein the ratio of average cell diameter to average cell opening diameter is about 3 to about 10; and
   a pad affixed to at least a portion of the foam.

2. The bandage of claim 1, wherein the cells have average diameters of about 40 to about 60 microns, the cell openings have average diameters of about 5 to about 15 microns, and the ratio of cell average diameter to cell opening average diameter is about 3 to about 5.

3. The bandage of claim 2, wherein the cell openings have average diameters of about 8 to about 15 microns, and the ratio of cell average diameter to cell opening average diameter is about 4.

4. The bandage of claim 1, wherein the cells are substantially spherical.

5. The bandage of claim 1, having a thickness of about 6 to about 20 mils, a tensile strength of greater than about 200 psi, a percent elongation of greater than about 120%, a tear strength of greater than about 10 pounds per linear inch, a tensile load at 20% elongation of less than about 100 pounds per square inch, an up water vapor transmission rate of greater than about 1,000 grams per square meter per day, and which does not leak water in a down water vapor transmission test.

6. The bandage of claim 1, having a thickness of about 8 to about 12 mils, a tensile strength of greater than about 350 psi, a percent elongation of greater than about 120%, a tear strength greater than about 15 pounds per linear inch, a tensile load at 20% elongation of less than about 70 pounds per square inch, and which does not leak water in a down water vapor transmission test.

7. The bandage of claim 6, having a density of about 25 to about 35 pounds per cubic foot, a tensile strength of greater than about 375 pounds per square inch, a percent elongation of greater than about 160%, a tear strength greater than about 20 pounds per linear inch, a tensile load at 20% elongation of less than about 60 pounds per square inch, an up water vapor transmission rate of greater than about 1,500 grams per square meter per day, and which does not leak water in a down water vapor transmission test.

8. The bandage of claim 6, having a density of about 28 to about 32 pounds per cubic foot, a tensile strength of greater than about 400 pounds per square inch, a percent elongation of greater than about 200%, a tear strength of greater than about 20 pounds per linear inch, a tensile load at 20% elongation of less than about 50 pounds per square inch, an up water vapor transmission rate of greater than about 2,000 grams per square meter per day, and which does not leak water in a down water vapor transmission test.

9. The bandage of claim 1, having a thickness of about 14 to about 18 mils, a tensile strength of greater than about 300 pounds per square inch, a percent elongation of greater than about 120%, a tear strength of greater than about 15 pounds per linear inch, a tensile load at 20% elongation of less than about 70 pounds per square inch, and which does not leak water in a down water vapor transmission test.

10. The bandage of claim 9, having a density of about 25 to about 35 pounds per cubic foot, a tensile strength of greater than about 325 pounds per square inch, a percent elongation of greater than about 160%, a tear strength of greater than about 20 pounds per linear inch, a tensile load at elongation of less than about 60 pounds per square inch, an up water vapor transmission rate of greater than about 1,500 grams per square meter per day, and which does not leak water in a down water vapor transmission test.

11. The bandage of claim 9, having a density of about 28 to about 32 pounds per cubic foot, a tensile strength of greater than about 350 psi, a percent elongation of greater than about 200%, a tear strength of greater than about 20 pounds per linear inch, a tensile load at elongation of less than about 50 pounds per square inch, an up water vapor transmission rate of greater than about 2,000 grams per square meter per day, and which does not leak water in a down water vapor transmission test.

12. The bandage of claim 1, having a density of about 28 to about 32 pounds per cubic foot, a tensile strength of greater than about 150 psi, a percent elongation of greater than about 160%, a tear strength of greater than about 20 pounds per linear inch, a tensile load at elongation of less than about 35 pounds per square inch, an up water vapor transmission rate of greater than about 2,000 grams per square meter per day, and which does not leak water in a down water vapor transmission test.

13. A polyurethane foam formed by foaming a mixture, comprising:
- a mixture comprising:
  - an organic polyisocyanate component;
  - an active hydrogen-containing component reactive with the polyisocyanate component;
  - a surfactant; and
  - a catalyst component; wherein the OH number of the mixture is from about 100 to about 180, and wherein the mixture has been frothed and cured into a foam, and
- wherein the cured foam has a density in the range from about 10 to about 40 pounds per cubic foot, cells with average diameters of about 20 to about 60 microns, and cell openings with average diameters of about 1 to about 25 microns, wherein the ratio of cell average diameter to cell opening average diameter is about 3 to about 10, and the molecular weight between cross-links is about 3,000 to 10,000.

14. The foam of claim 13, wherein foaming is by mechanical frothing.

15. The foam of claim 13, wherein the organic polyisocyanate component is a polymeric diphenylmethane-4,4'-diisocyanate having an average isocyanate functionality from 2.00 to 2.25.

16. The foam of claim 13, wherein the organic polyisocyanate component is a polymeric diphenylmethane-4,4'-diisocyanate having an average isocyanate functionality of 2.2.

17. The foam of claim 13, wherein the active hydrogen-containing component comprises a polyether polyol and a polyester polyol.

18. The foam of claim 17, wherein the ratio of polyisocyanate to active hydrogen is from 0.8 to 1.2.

19. The foam of claim 13, wherein the ratio of polyisocyanate to active hydrogen is from 1.0 to 1.05.

20. The foam of claim 13, wherein the cells have an average diameter of about 40 to about 60 microns, the cell openings have an average diameter of about 5 to about 15 microns, and the ratio of average cell diameter to average cell opening diameter is about 3 to about 5.

21. The foam of claim 13, wherein the cell openings have an average diameter of about 8 to about 15 microns, and the ratio of average cell diameter to average cell opening diameter is about 4.

22. The foam of claim 13, wherein the cells are substantially spherical.

23. The foam of claim 13, having a thickness of about 6 to about 20 mils, a tensile strength of greater than about 200 psi, a percent elongation of greater than about 120%, a tear strength of greater than about 10 pounds per linear inch, a tensile load at 20% elongation of less than about 100 pounds per square inch, an up water vapor transmission rate of greater than about 1,000 grams per square meter per day, and which does not leak water in a down water vapor transmission test.

24. The foam of claim 13, having a thickness of about 8 to about 12 mils, a tensile strength of greater than about 350 psi, a percent elongation of greater than about 120%, a tear strength greater than about 15 pounds per linear inch, a tensile load at 20% elongation of less than about 70 pounds per square inch, and which does not leak water in a down water vapor transmission test.

25. The foam of claim 24, having a density of about 25 to about 35 pounds per cubic foot, a tensile strength of greater than about 375 pounds per square inch, a percent elongation of greater than about 160%, a tear strength greater than about 20 pounds per linear inch, a tensile load at 20% elongation of less than about 60 pounds per square inch, an up water vapor transmission rate of greater than about 1,500 grams per square meter per day, and which does not leak water in a down water vapor transmission test.

26. The foam of claim 25, having a density of about 28 to about 32 pounds per cubic foot, a tensile strength of greater than about 400 pounds per square inch, a percent elongation of greater than about 200%, a tear strength of greater than about 20 pounds per linear inch, a tensile load at 20% elongation of less than about 50 pounds per square inch, an up water vapor transmission rate of greater than about 2,000 grams per square meter per day, and which does not leak water in a down water vapor transmission test.

27. The foam of claim 13, having a thickness of about 14 to about 18 mils, a tensile strength of greater than about 300 pounds per square inch, a percent elongation of greater than about 120%, a tear strength of greater than about 15 pounds per linear inch, a tensile load at 20% elongation of less than about 70 pounds per square inch, and which does not leak water in a down water vapor transmission test.

28. The foam of claim 27, having a density of about 25 to about 35 pounds per cubic foot, a tensile strength of greater than about 325 pounds per square inch, a percent elongation of greater than about 160%, a tear strength of greater than about 20 pounds per linear inch, a tensile load at elongation of less than about 60 pounds per square inch, an up water vapor transmission rate of greater than about 1,500 grams per square meter per day, and which does not leak water in a down water vapor transmission test.

29. The foam of claim 28, having a density of about 28 to about 32 pounds per cubic foot, a tensile strength of greater than about 350 psi, a percent elongation of greater than about 200%, a tear strength of greater than about 20 pounds per linear inch, a tensile load at elongation of less than about 50 pounds per square inch, an up water vapor transmission rate of greater than about 2,000 grams per square meter per day, and which does not leak water in a down water vapor transmission test.

30. The foam of claim 13, having a density of about 28 to about 32 pounds per cubic foot, a tensile strength of greater than about 150 psi, a percent elongation of greater than about 160%, a tear strength of greater than about 20 pounds per linear inch, a tensile load at elongation of less than about 35 pounds per square inch, an up water vapor transmission rate of greater than about 2,000 grams per square meter per day, and which does not leak water in a down water vapor transmission test.

* * * * *